(12) United States Patent
Feld et al.

(10) Patent No.: US 7,901,349 B2
(45) Date of Patent: Mar. 8, 2011

(54) ENDOSCOPE REPROCESSOR CONNECTIVITY APPARATUS AND METHOD

(75) Inventors: Paul T. Feld, Buffalo, MN (US); Michael P. Petersen, Eden Prairie, MN (US); John E. Marxer, Eagan, MN (US); Ward J. Sly, Brooklyn Park, MN (US); Johannes Antonius Walta, Leidschenoam (NL)

(73) Assignee: Minntech Corporation, Minneapolis, MN (US)

( * ) Notice: Subject to any disclaimer, the term of this patent is extended or adjusted under 35 U.S.C. 154(b) by 1273 days.

(21) Appl. No.: 11/264,909

(22) Filed: Nov. 2, 2005

(65) Prior Publication Data

US 2007/0100204 A1    May 3, 2007

(51) Int. Cl.
*A61B 1/00*    (2006.01)
*A61B 1/015*    (2006.01)

(52) U.S. Cl. .......................... 600/155; 600/158; 600/117

(58) Field of Classification Search .................. 600/117, 600/118, 156, 158, 159, 155; 73/46, 49.2, 73/49.3, 40

See application file for complete search history.

(56) References Cited

U.S. PATENT DOCUMENTS

| | | | |
|---|---|---|---|
| 5,091,343 A | | 2/1992 | Schneider et al. |
| 5,279,799 A | * | 1/1994 | Moser ............................ 422/292 |
| 5,367,797 A | * | 11/1994 | Zaim ............................... 73/49.2 |
| 5,494,530 A | * | 2/1996 | Graf ................................. 134/18 |
| 5,738,824 A | * | 4/1998 | Pfeifer .............................. 422/3 |
| 5,761,069 A | | 6/1998 | Weber et al. |
| 6,047,431 A | | 4/2000 | Canonica |
| 6,068,815 A | | 5/2000 | Oberleitner et al. |
| 6,203,767 B1 | | 3/2001 | Leasko |
| 6,260,560 B1 | | 7/2001 | Walta |
| 6,408,682 B2 | | 6/2002 | Greszler |
| 6,412,334 B1 | * | 7/2002 | Kral et al. ......................... 73/40 |
| 6,585,934 B1 | | 7/2003 | Oberleitner et al. |
| 6,641,781 B2 | | 11/2003 | Walta |
| 6,824,751 B2 | | 11/2004 | Rossell |
| 6,848,456 B2 | | 2/2005 | Weber |
| 6,860,276 B2 | | 3/2005 | Weber |

(Continued)

FOREIGN PATENT DOCUMENTS

DE    10321991    5/2004

(Continued)

OTHER PUBLICATIONS

International Search Report and Written Opinion of international application No. PCT/US2006/060389, filed Oct. 31, 2006, mailed Dec. 13, 2007, 13 pp.

(Continued)

*Primary Examiner* — John P Leubecker
(74) *Attorney, Agent, or Firm* — Faegre & Benson LLP

(57) ABSTRACT

Apparatus and method for detecting connectivity in a channel in an endoscope undergoing reprocessing using an automatic reprocessor, the apparatus including a source of pressurized fluid which may be a gas alone or gas and liquid and a back pressure detector connected to the channel or channels of interest in the endoscope, the method including providing a source of pressurized fluid, directing the pressurized fluid to a channel in an endoscope, monitoring the time for the back pressure in the pressurized fluid to decay to a predetermined level; and determining whether the channel is connected and open or disconnected by comparing the decay time of the actual back pressure to one or more predetermined values corresponding to the specific channel or channels and model of endoscope undergoing reprocessing.

20 Claims, 14 Drawing Sheets

U.S. PATENT DOCUMENTS

| | | | |
|---|---|---|---|
| 6,915,810 B2 | 7/2005 | Weber | |
| 6,986,736 B2 * | 1/2006 | Williams et al. | 600/101 |
| 7,290,440 B2 * | 11/2007 | Gocho | 73/49.2 |
| 7,340,943 B2 * | 3/2008 | Jackson et al. | 73/49.2 |
| 2004/0091391 A1 | 5/2004 | Walta | |
| 2004/0118413 A1 * | 6/2004 | Williams et al. | 128/898 |
| 2004/0118437 A1 * | 6/2004 | Nguyen | 134/22.11 |
| 2004/0139789 A1 * | 7/2004 | Masters | 73/49.2 |
| 2005/0056081 A1 * | 3/2005 | Gocho | 73/40 |
| 2005/0065405 A1 | 3/2005 | Hasegawa | |
| 2005/0079094 A1 * | 4/2005 | Mariotti et al. | 422/3 |
| 2005/0148819 A1 * | 7/2005 | Noguchi et al. | 600/133 |
| 2006/0047186 A1 * | 3/2006 | Annecke | 600/159 |
| 2006/0224042 A1 * | 10/2006 | Jackson et al. | 600/133 |
| 2007/0089487 A1 * | 4/2007 | Jackson et al. | 73/37 |
| 2007/0100203 A1 * | 5/2007 | Jackson et al. | 600/117 |
| 2007/0100206 A1 * | 5/2007 | Lin et al. | 600/156 |

FOREIGN PATENT DOCUMENTS

| | | |
|---|---|---|
| EP | 0 709 056 A1 | 5/1996 |
| EP | 1338237 | 8/2003 |
| WO | WO 00/45859 | 8/2000 |
| WO | 03056291 | 7/2003 |

OTHER PUBLICATIONS

Mar. 13, 2008, English translation of description and claims of EP1338237, first cited in the International Search Report mailed Dec. 13, 2007, for corresponding international application PCT/US2006/060389.

Mar. 13, 2008, English translation of description and claims of DE10321991, first cited in the International Search Report mailed Dec. 13, 2007, for corresponding international application PCT/US2006/060389.

US 5,882,859, 03/1999, Mariotti (withdrawn)

* cited by examiner

# ENDOSCOPE REPROCESSOR CONNECTIVITY APPARATUS AND METHOD

BACKGROUND OF THE INVENTION

This invention relates to the field of reprocessors for devices, particularly medical devices, and more particularly to endoscopes and the like having one or more internal passageways which are to be cleaned and disinfected by an automatic reprocessor. Reprocessing includes washing, disinfecting and drying such devices. As used herein, the terms "endoscope" and "endoscopes" refer not only to endoscopes, but also to similar devices (including accessories) which may suitably be reprocessed using an Automatic Endoscope Reprocessor, or AER.

In the past, AERs typically relied upon the human operator to properly connect and inspect the connections between the endoscope and the AER.

In the prior art, it was known to pressurize the sheath of an endoscope to test for leaks. In that type of test, if any leakage was measured, the endoscope under test was required to be serviced, since such testing was directed to a closed system in which it was expected and desired to have no leakage. However, with the present invention, testing for connectivity of channels in the endoscope must take leakage into account, since the distal end of the endoscope characteristically has one or more channel openings which will inherently (and properly) leak when the channel or channels are subjected to pressurized fluid. As such, conventional leak testing techniques of the prior art are not suitable for connectivity testing according to the present invention.

Endoscopes which are candidates for the present invention include various configurations for through passages or channels, small non-interconnected channels, large non-interconnected channels, interconnected passages having at least one small channel, and interconnected passages having only large channels.

SUMMARY OF THE INVENTION

The present invention surmounts shortcomings of the prior art by providing apparatus and method to automatically and efficiently detect whether a proper connection exits between the reprocessor and the endoscope or whether there are any missing connections (i.e., disconnection) between a specific channel in the endoscope and the AER.

In one aspect, the present invention utilizes a tank which may be pressurized with a suitable fluid (which may be a gas such as air in one or more embodiments), and discharged through an endoscope being reprocessed with a characteristic time to discharge monitored. In another embodiment, a charge or "slug" of liquid is either already present in or delivered to the endoscope and is thereafter combined with the gaseous fluid and discharged through an endoscope being reprocessed, with a characteristic time to discharge monitored. With either embodiment, the present invention determines whether the path or channel is disconnected or connected and open.

In another aspect, the fluid is used to detect connectivity and a pump may be used to deliver the fluid to respective paths in the endoscope, with the time monitored to determine when (and if) the pressure drops to a predetermined pressure level, and if the pressure does so drop, a comparison is made to characteristic times corresponding to the conditions in which the path or channel is disconnected or connected and open.

In still another aspect, a full shutoff connector may be used with large channels to "reverse" the logic for determining whether the large channel is disconnected, or connected to the reprocessor and open.

In yet another aspect, for configurations having at least some large interconnected channels, pressurized liquid is applied to one large channel, and back pressure is monitored in another large channel interconnected therewith to determine whether the respective channels monitored are disconnected or connected and open.

DETAILED DESCRIPTION OF THE INVENTION

One example of a system for cleaning, disinfecting and/or drying endoscopes is shown in U.S. Pat. No. 6,641,781 B2, issued Nov. 4, 2003, and the entire contents thereof are hereby incorporated by reference.

Another example of a device and method for cleaning and/or disinfecting endoscopes is shown in U.S. Pat. No. 6,260,560 B1, issued Jul. 17, 2001, and the entire contents thereof are hereby incorporated by reference.

Still another example of a device and method for cleaning and/or disinfecting endoscopes is shown in European Patent Application EP 0 709 056 A1, published 01.05.1996, and the entire contents thereof are hereby incorporated by reference.

Figure 1:
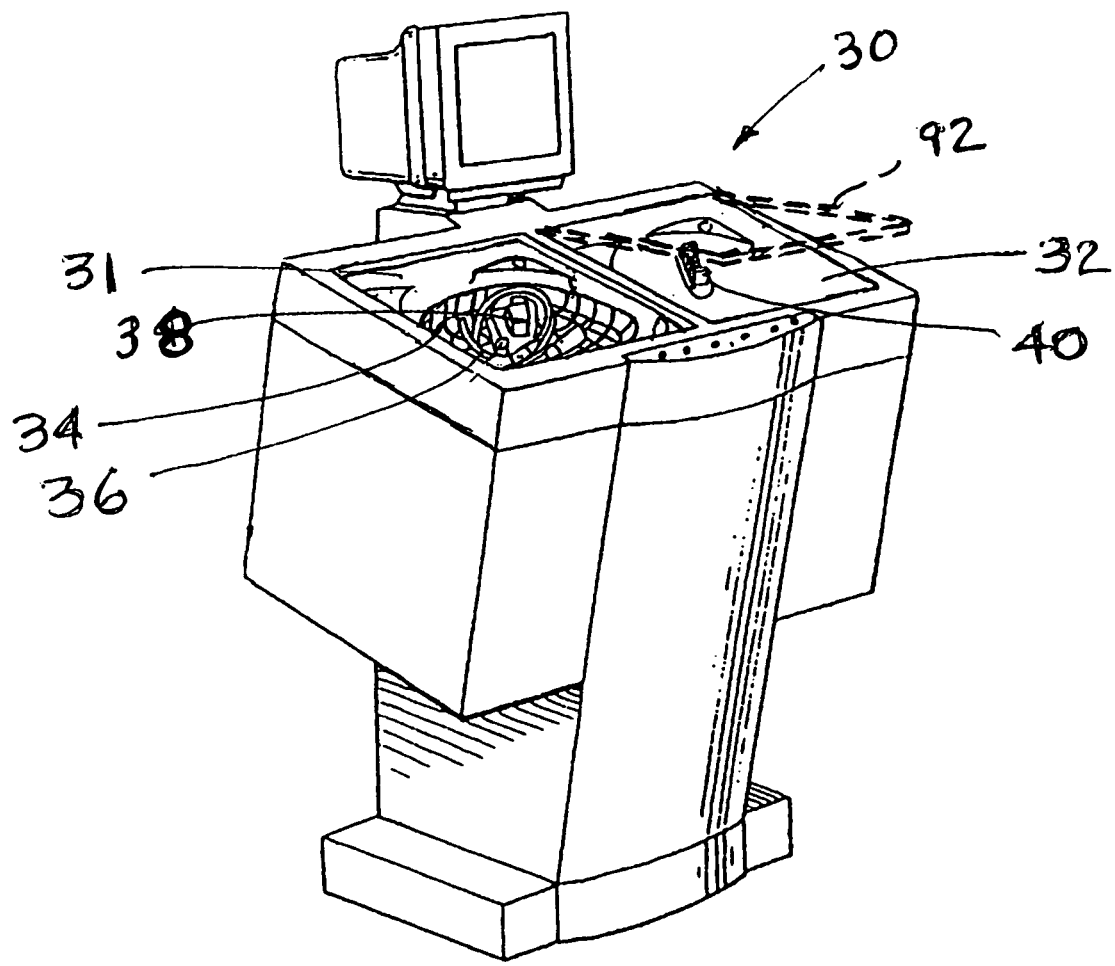
FIG. 1 is a very diagrammatic view in perspective of a prior art Automatic Endoscope Reprocessor useful in the practice of the present invention.

Referring now most particularly to FIG. 1, a disinfecting device or Automatic Endoscope Reprocessor (or AER) 30 may be seen. The disinfecting device 30 is provided with two trays or basins 31 and 32 in which a rack 34 is, with an endoscope 36 therein, can be accommodated. In FIG. 1, a rack of this nature is located in the left hand tray. Each of trays 31 and 32 are provided with a counter-connection block which, when a rack 34 is placed in the tray 31 or 32, can be connected to the connection block 38 arranged in rack 34. The counter-connection block arranged in the right hand tray or basin 31 can be seen in FIG. 1 and is denoted by the reference numeral 40. A lid 92 is shown in a partially open condition over right basin 32.

Figure 2:
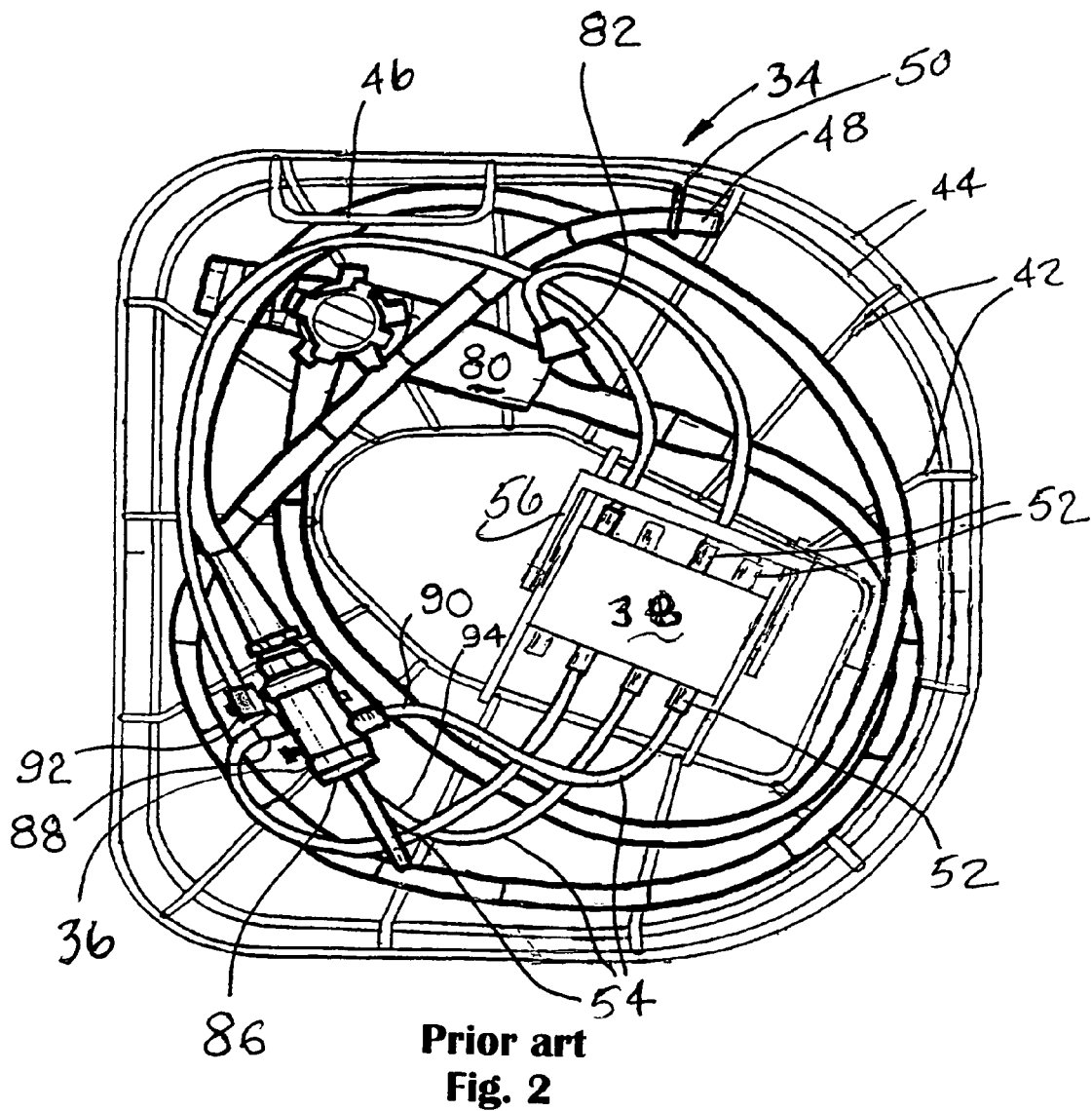
FIG. 2 is a plan view of a prior art rack with an endoscope therein suitable for use with the apparatus of FIG. 1.

Referring now also to FIG. 2, the rack 34 may be formed from bent rods 42 and 44 which are fixedly connected to one another. The rack 34 is provided with one or two handles 46, by means of which the rack can be gripped and lifted up. The rack 34 is furthermore formed in such a manner that an endoscope 36 can be placed therein in a more or less folded state. In order to be able to fix in particular the fragile end 48 of the endoscope, the rack may be provided with a tip holder 50. One example of a connection made between the reprocessor 30 and the endoscope 36 is illustrated by a biopsy channel connector 82.

The connection block 38 is arranged fixedly in the rack. This connection block is provided with passages and ports 52 which can be connected to the passages of the endoscope 36 by means of flexible tubes 54. On its underside (not visible in Figure. 2), the connection block 38 is provided with connection points for the connection of the counter-connection block in either basin 31 or 32 of device 30. The connection block 38 is furthermore provided with a handle 56. By moving the handle 56, the connection block 38 can be connected to a counter-connection block or removed therefrom.

Figure 3:
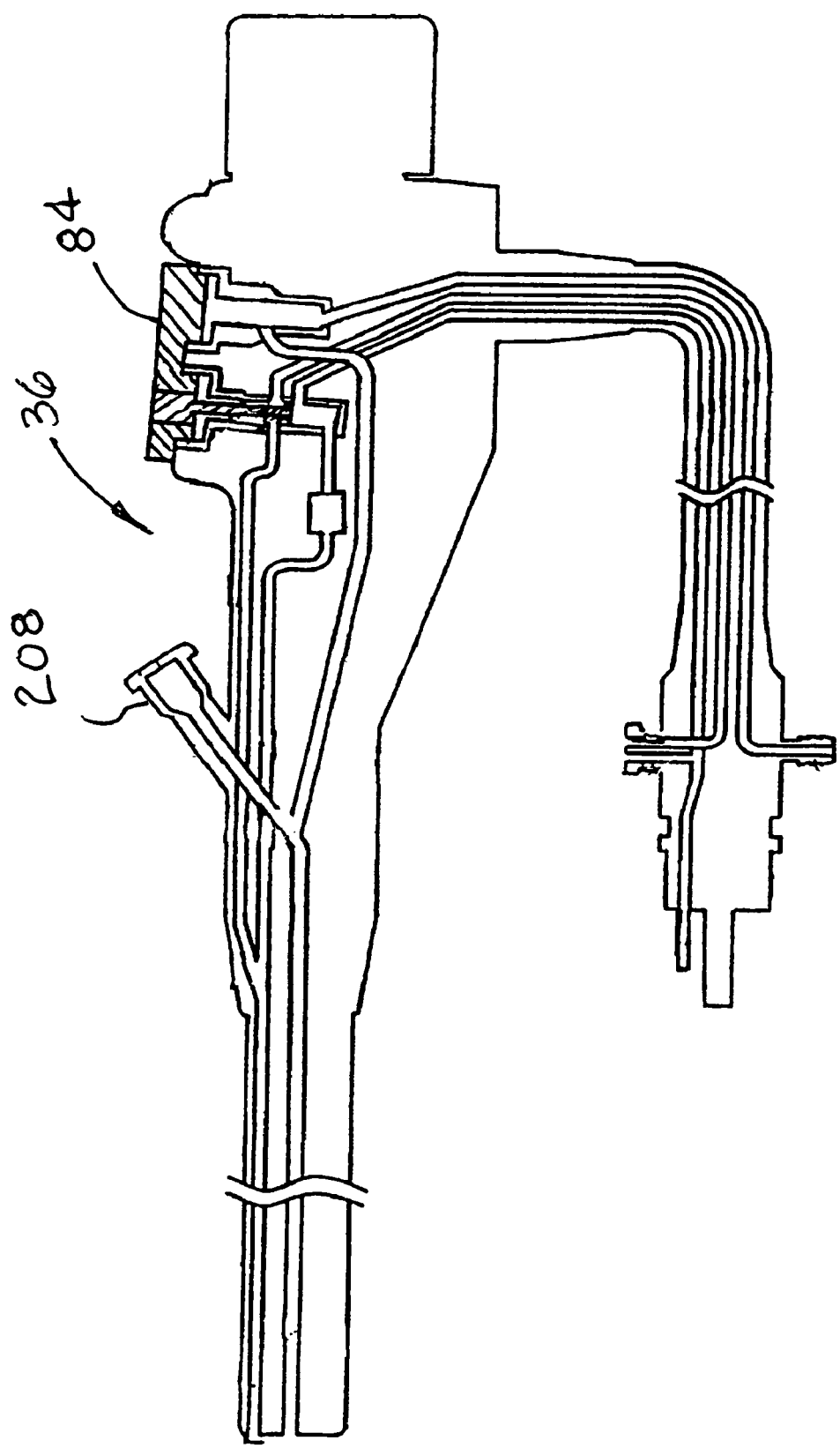
FIG. 3 is simplified diagrammatic view of a certain prior art type of endoscope suitable for reprocessing in the practice of the present invention.
Figure 4:
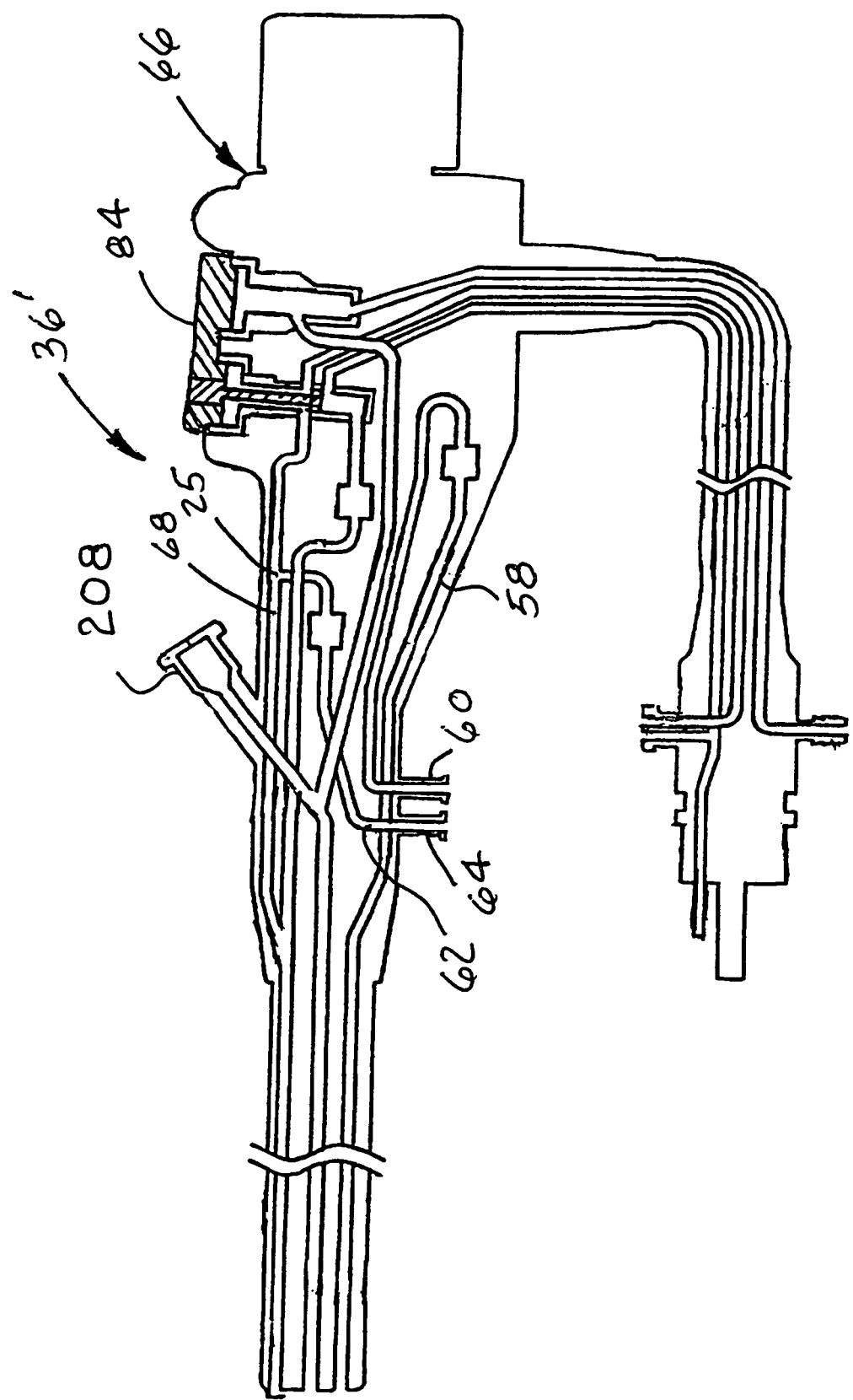
FIG. 4 is a simplified diagrammatic view of another prior art type of endoscope suitable for reprocessing in the practice of the present invention.

Referring now to FIGS. 3 and 4, examples of different types of endoscopes 36, 36' to be reprocessed by the device 30 may be seen. Endoscope 36 is a first type of endoscope and endoscope 36' is a second type of endoscope differing from the first type of endoscope 36 in that it is provided with an additional channel 58 with connection 60 and an additional channel 62 with connection 64. In a head part 66, the channel 62 is connected to an air channel 68 at a joining part 25. A biopsy channel fitting 208 may be seen in FIGS. 3 and 4 to which the connector 82 is attached in FIG. 2.

Figure 5:
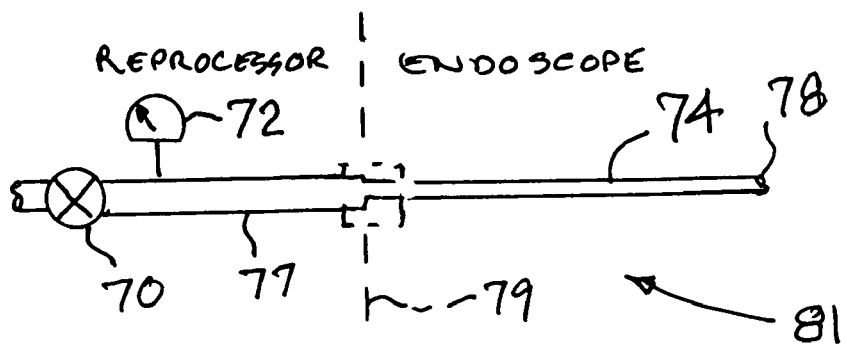
FIG. 5 is a very simplified set of connection paths between the reprocessor and various channel configurations to illustrate various applications of the present invention.
Figure 5:
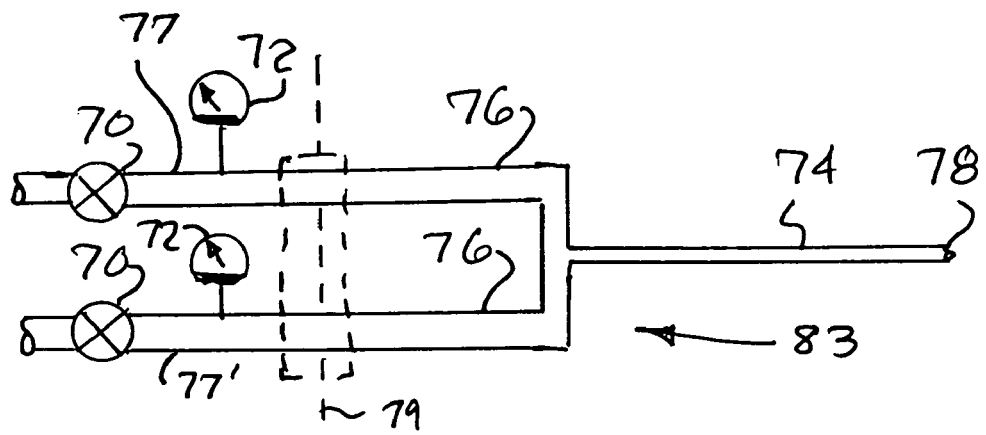
Figure 5:
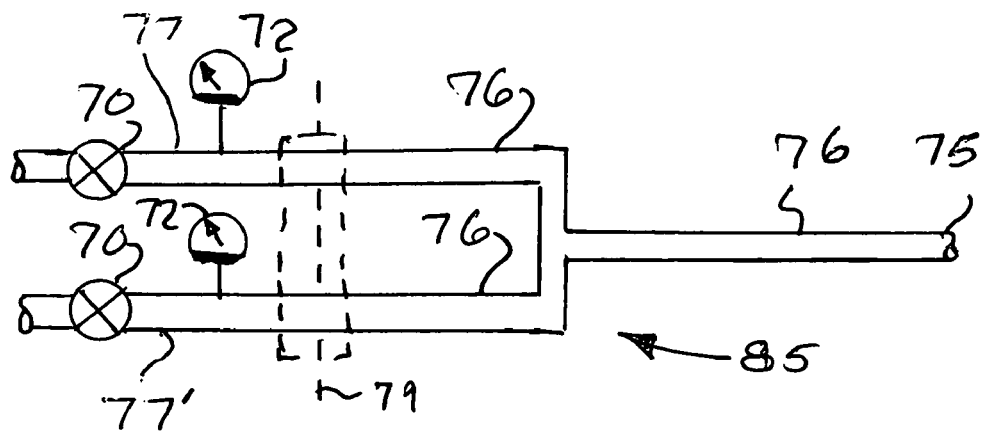
Figure 5:
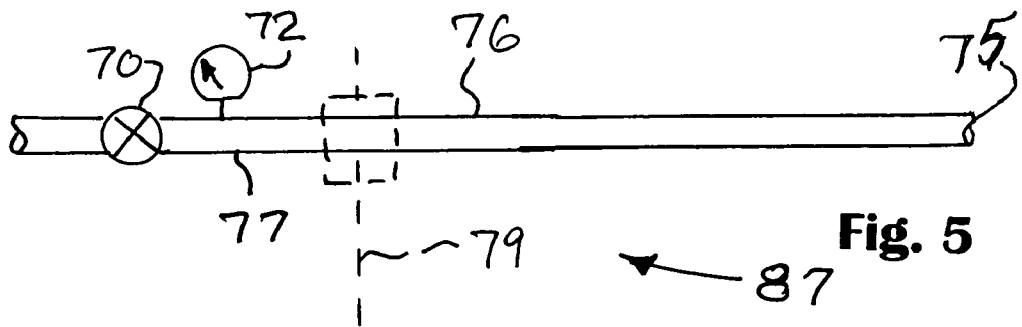

Referring to FIG. 5, very simplified views of channel configurations to be tested for connectivity may be seen. These include: a. configuration 81, an independent small channel 74, b. configuration 83 which shows an interconnected pathway with one or more large channels 76 and a small channel 74, c. configuration 85 of an interconnected pathway with (only) three large channels 76, and d. a pathway or configuration 87 with only an independent large channel 76. It is to be understood that in configurations 81 and 83, the small channel 74 in the endoscope has a distal end 78 open to atmosphere, and in configurations 85 and 87 the large channel 76 in the endoscope has a distal end 75 open to atmosphere. The dashed line 79 indicates the interface between the reprocessor 30 and the endoscope 36 under test and includes the connection made between the connection block 38 and the counter connection block 40 (see FIG. 1), along with respective flexible tubes 54 (see FIG. 2). In each of these arrangements, one or more valves 70 (which may be understood to correspond to valves 96 in FIG. 6, described infra) and one or more pressure sensors 72 (which may be understood to correspond to switches 98 in FIG. 6, described infra) are provided in the reprocessor side. Pressure sensors 72 preferably have an adjustable trip point preset to a predetermined pressure level, for example 2 psi. In the top diagram (configuration 81) in FIG. 5, it has been found preferable to have the feed line 77 be 3 mm in diameter when the diameter of the small channel is about 0.5 mm.

In configuration 81 or 83, connectivity may be determined according to the first embodiment of the present invention wherein a pressurized gaseous fluid is delivered to the endoscope and the time of decay of pressure is monitored to determine the connectivity conditions of connected and open or disconnected.

In configuration 83 or 85, it is also possible to measure connectivity in a second embodiment by filling all channels with liquid under pressure (using, for example, a pump supplying water continuously through feed line 77) and measuring back pressure in the other reprocessor channel 77' (with the valve 70 in line 77' closed) to determine whether the endoscope is connected or not. If back pressure exceeds a predetermined level, both reprocessor channels 77 and 77' are connected to the endoscope channels 76. If pressure is applied in channel 77 and back pressure is absent in channel 77' (as indicated by pressure sensor 72 connected to channel 77') the system will determine that a blockage exists in one or both of channels 77 and 77' or that channel 77 or channel 77' (or both) are disconnected, each of which conditions require that reprocessing be interrupted and the condition appropriately corrected.

In configurations 85 and 87, it is also possible to measure connectivity using a liquid (preferably water) "slug" to test the channels, whether they are large interconnected channels (as in configuration 85) or a non-interconnected large channel (as in configuration 87).

Finally, with configuration 87 it is also possible to use a full shutoff connector (described infra with respect to FIGS. 14-16) in an alternative embodiment of the present invention.

Figure 6:
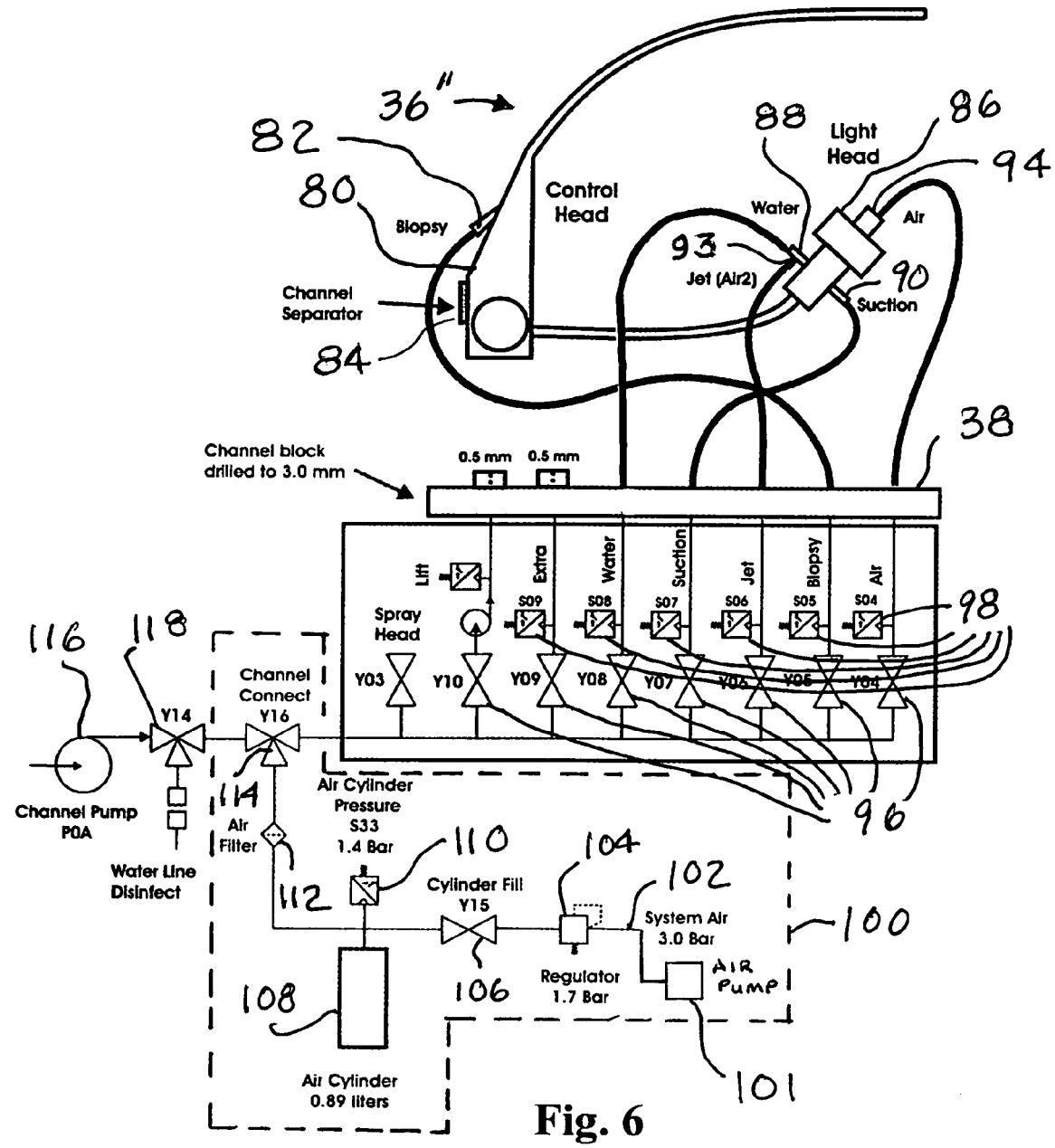
FIG. 6 is a simplified schematic flow path with a particular endoscope connected to a reprocessor in one embodiment of the present invention.

Referring now to FIG. 6, a less simplified schematic showing connections to a specific model of endoscope 36" (similar to endoscopes 36 and 36') for carrying out the present invention in one embodiment may be seen. Endoscope 36" has a control head 80 including a biopsy fitting on which is received the connector 82. Endoscope 36" also has a channel separator 84 installed, the details of which may be seen in FIGS. 3 and 4. Endoscope 36" also has a light head 86 with a water connector 88, a suction connector 90, a jet connector 93, and an air connector 94. This embodiment of the present invention uses a conventional connection block 38 to connect to the endoscope 36." In the AER there are respective valves 96 (corresponding to valves 70 in FIG. 5) and pressure switches 98 (corresponding to pressure sensors 72 in FIG. 5). One valve 96 and switch 98 are associated (respectively) with each port 52 and line 54 that may be connected to the endoscope 36." It is to be understood that more or fewer connections than those shown may be used in the practice of the present invention, depending on the complexity of the endoscope to be reprocessed.

In the embodiment shown in FIG. 6, the parts included within dashed line 100 have been added to carry out the first embodiment of the present invention. In the first embodiment, an air pump 101 provides air at line 102. Air pump 101 may be a double action reciprocating pump. Alternatively, air may be supplied as system air from a source of pressurized air in the facility in which the AER is installed. Pressurized air at line 102 may be passed through a regulator 104 which may be used to maintain an operating air pressure, which in the embodiment shown is 1.7 bar. A CYLINDER FILL valve 106 may be selectively operated to charge an air cylinder 108, which, in one embodiment may have a capacity of 0.89 liters. An air cylinder pressure switch 110 may be used to confirm that the air pressure in the cylinder is above a predetermined pressure, preferably 1.4 bar. An air filter 112 and a CHANNEL CONNECT VALVE 114 may be used to complete the connectivity system components in system 100. Valve 114 may connect either water from a channel pump 116 or air from the air cylinder 108, under the system control (not shown).

In operation with the first embodiment using a gaseous fluid such as air, a channel to be tested for connectivity is first purged of liquid, if necessary, and then the channel connect valve 114 is closed, and the air cylinder 108 is charged to a predetermined volume and pressure, after which the channel connect valve 114 is opened to admit air from the cylinder 108, it being understood that the endoscope is in place in the rack 34 in the AER 30 with the connection block 38 in fluid communication with the counter connection block 40. One of valves 96 is opened (either at the same time or after valve 114 is opened) and the time to discharge the particular channel in the endoscope 36" is monitored by the pressure switch 98 associated with and in fluid communication with the valve 96 that is opened. When the pressure drops to a predetermined level, for example, 2 psi, the time to reach that level is recorded by the control, and a determination is made whether that channel of the endoscope 36" is connected to its respective port 52 or whether the channel is disconnected from its port 52. It is to be understood that the characteristic time to discharge for each channel is measured and stored in the control of the AER 30. If the time to actually discharge through the channel is shorter than the characteristic time for that channel, the endoscope is disconnected and an error signal indicating CHANNEL DISCONNECTED is given to the operator. If the actual time to discharge through the channel is equal to the characteristic time for that channel (within empirically determined tolerances) the AER 30 determines that the channel is connected and open.

It is to be understood that in addition to configuration 81, configuration 83 may also be tested using the above described embodiment in which case each of feed lines 77 and 77' may be tested independently by shutting off one and testing the other, or by monitoring both pressure sensors 72 while supplying gaseous fluid to one line (e.g., line 77), while the other (77' in this example) has its respective inlet valve 70 shut off. If both pressure sensors 72 reach the predetermined trip point pressure at about the characteristic time for this configuration, both channels are connected and open. If the time to reach the predetermined trip point pressure is less than the characteristic time, one or both channels are disconnected and an appropriate indication is given to the operator to check both channels 76 for connection to the reprocessor.

Figure 7:
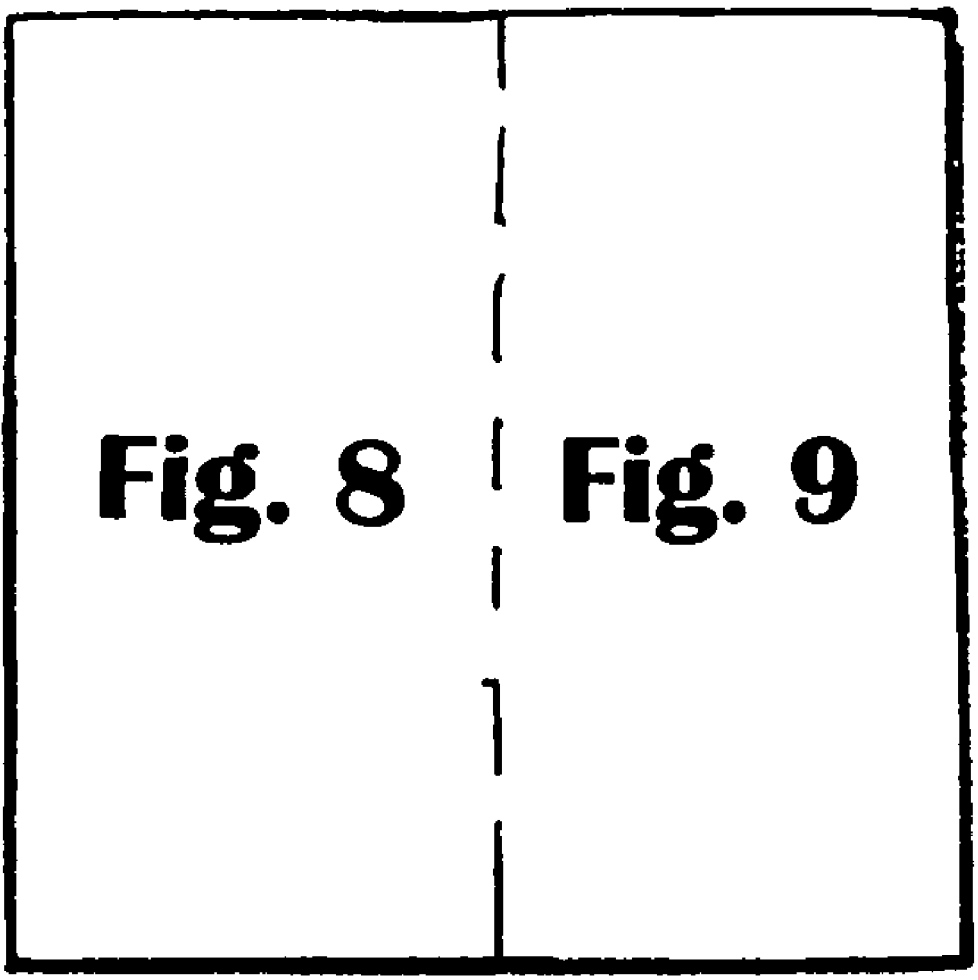
FIG. 7 is a key for FIGS. 8 and 9.
Figure 8:
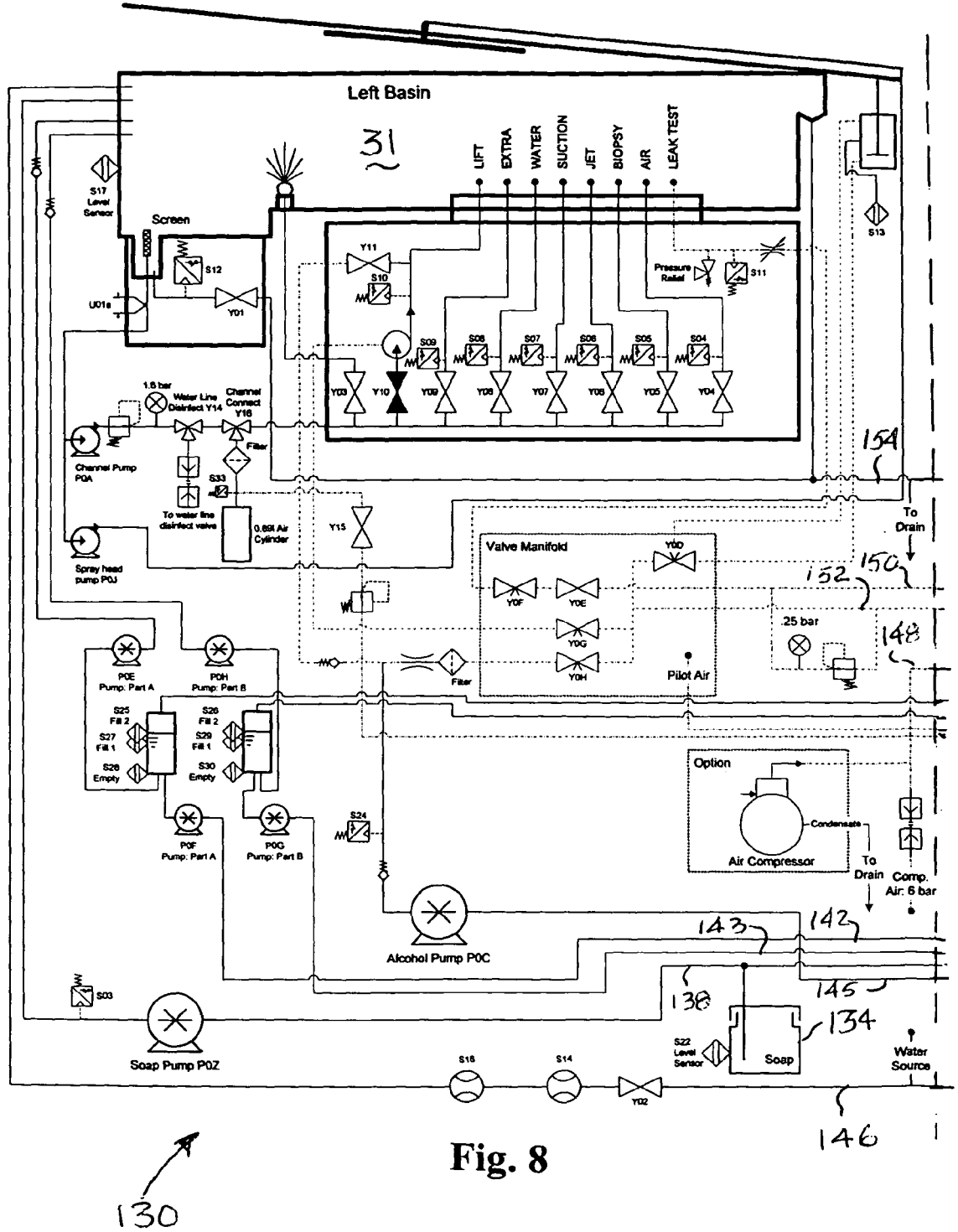
FIG. 8 is a first portion of an example hydraulic schematic for a reprocessor useful in the practice of the present invention.
Figure 9:
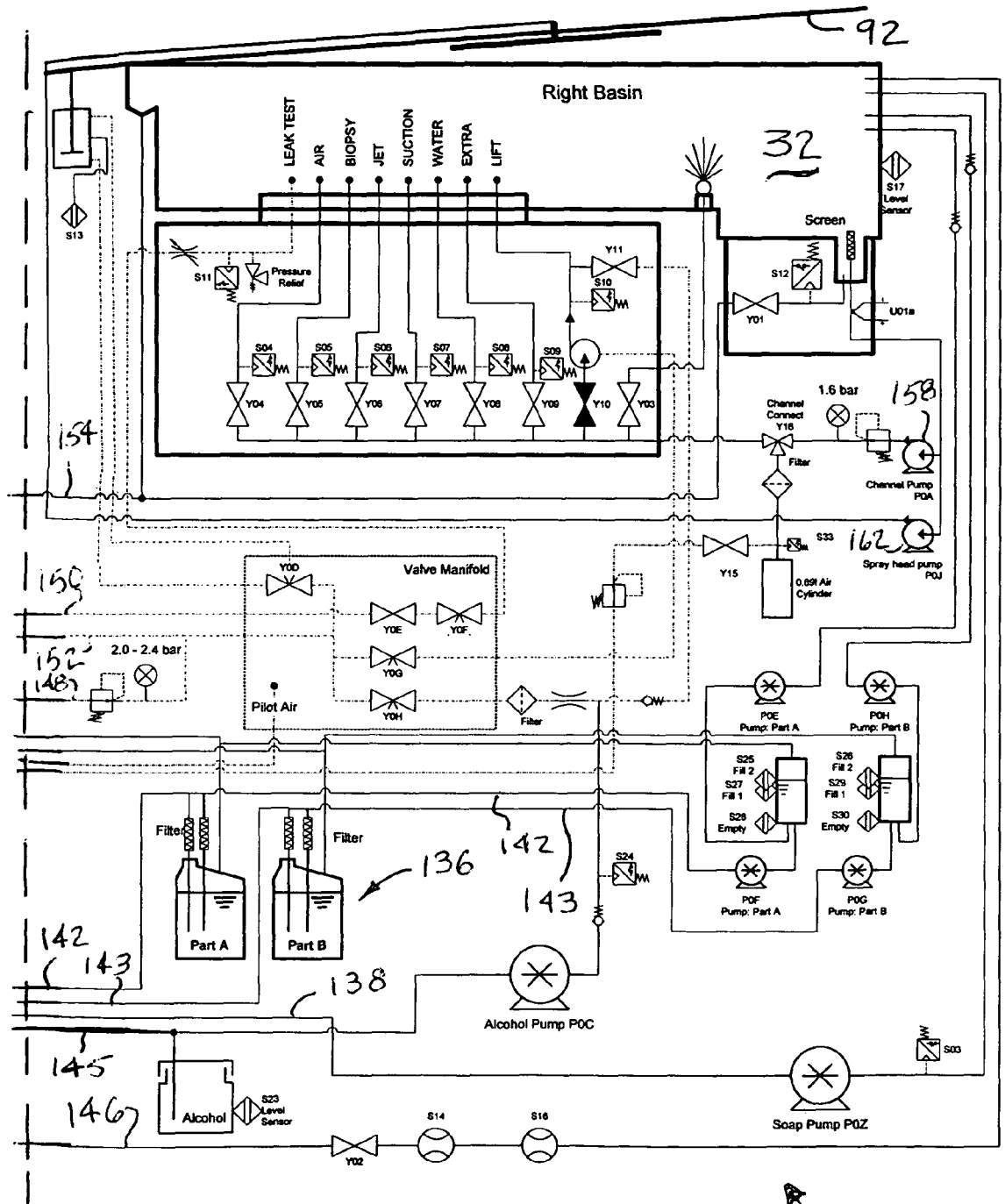
FIG. 9 is a second portion of the schematic of FIG. 8.

Referring now to FIGS. 7, 8 and 9, a hydraulic schematic for the practice of the present invention may be seen. FIG. 7 is a key to illustrate the arrangement of FIGS. 8 and 9. FIG. 8 is a schematic or circuit 130 for the left basin 31, and FIG. 9 is a schematic or circuit 132 for the right basin 32. Lid 92 is shown schematically in FIG. 9. It is to be understood that both a soap reservoir 134 and a pair of disinfectant reservoirs 136 are shared by each circuit 130 and 132. Circuits 130 and 132 also use a shared soap supply line 138. Circuits 130 and 132 share a pair of disinfectant supply lines 142 and 143. It may be also be seen that circuits 130 and 132 are joined at and share the following connections: a water source line 146, a compressed air source line 148, a lower pressure air line 150, preferably supplying air at 0.25 bar, for example, and a higher pressure air line 152 preferably supplying air at 2.0 to 2.4 bar, for example. Circuits 130 and 132 may also share a common drain connection line 154 and a common alcohol supply line 145. It is to be understood that the apparatus shown in FIGS. 8 and 9 is preferably contained within the enclosure of device 30 shown in FIG. 1.

Figure 10:
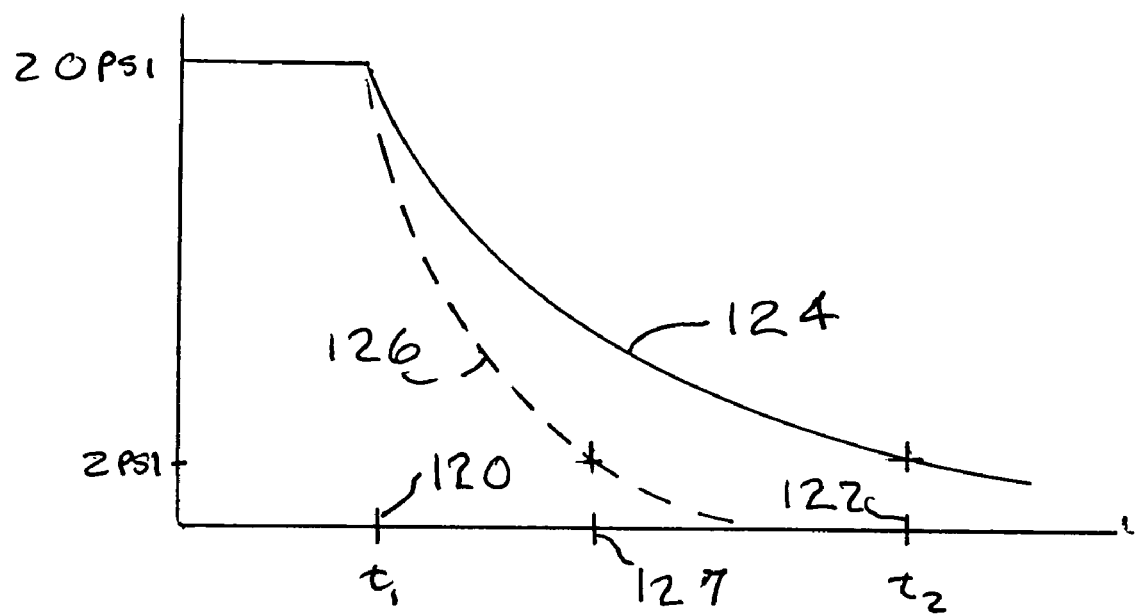
FIG. 10 is a pressure versus time waveform illustrating certain aspects of the present invention.

FIG. 10 illustrates more detail about the first embodiment of the present invention in which the system 100 of FIG. 6 is used. Valve 114 is opened to air from cylinder 108 at a pressure of 20 psi at time $t_1$ 120 and the incremental time from $t_1$ 120 to $t_2$ 122 is measured, by monitoring the appropriate switch 98, set to trip at 2 psi. The actual time ($t_{actual} = t_2 - t_1$) is compared to the previously recorded characteristic time $t_{CHAR}$ to determine the connectivity condition of the channel under test. The solid line curve 124 illustrates the pressure decay for a connected and open (unblocked) channel, while dashed line 126 represents a disconnected channel, with switch 98 activating at time 127.

The above described operation will be satisfactory with most small channels because there is a considerable difference between the connected and disconnected conditions. In addition some connectors used for certain small channels (for example the Lift channels and some Jet channels) have additional restriction which tends to decrease the separation between disconnected and connected conditions.

Figure 12:
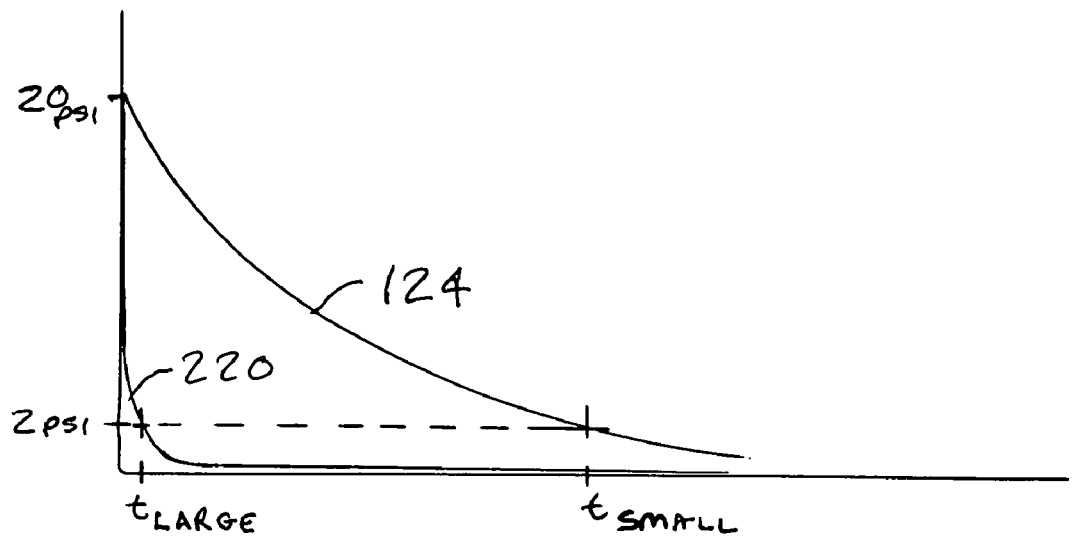
FIG. 12 is a pressure versus time waveform illustrating pressure decay characteristics of large and small channels in connection with the practice of the present invention.

Referring now also to FIG. 12, a characteristic curve 220 for a large channel pressure decay may be seen in comparison to a corresponding characteristic curve for a small channel pressure decay, e.g., curve 124. It is to be understood that curve 220 can be taken to represent both connected and disconnected conditions for a large independent channel, because large channels characteristically have low flow restriction and little difference between connected and disconnected conditions and thus do not have enough separation between connected and disconnected conditions to allow the technique of using a flow restriction threshold to be reliable. However, since there are only a small number of types of connectors required to connect to large channels, one approach can be to provide connectors which shut off fluid flow when disconnected. In this type of connector, flow is shut off when the channel is disconnected, and full, generally unrestricted, flow is permitted or enabled when the connector is coupled together and the channel is connected to the AER. A connector with full shutoff when the endoscope channel is disconnected allows a reversal of the logic conditions on whether disconnected or connected conditions restrict flow more. That is (for example) with a full shutoff connector, when the large channel is connected, there is no or little restriction to flow, but when the large channel is disconnected, the full shutoff connector will block flow, allowing detection of the disconnected condition for the large channel.

Figures 14, 15:
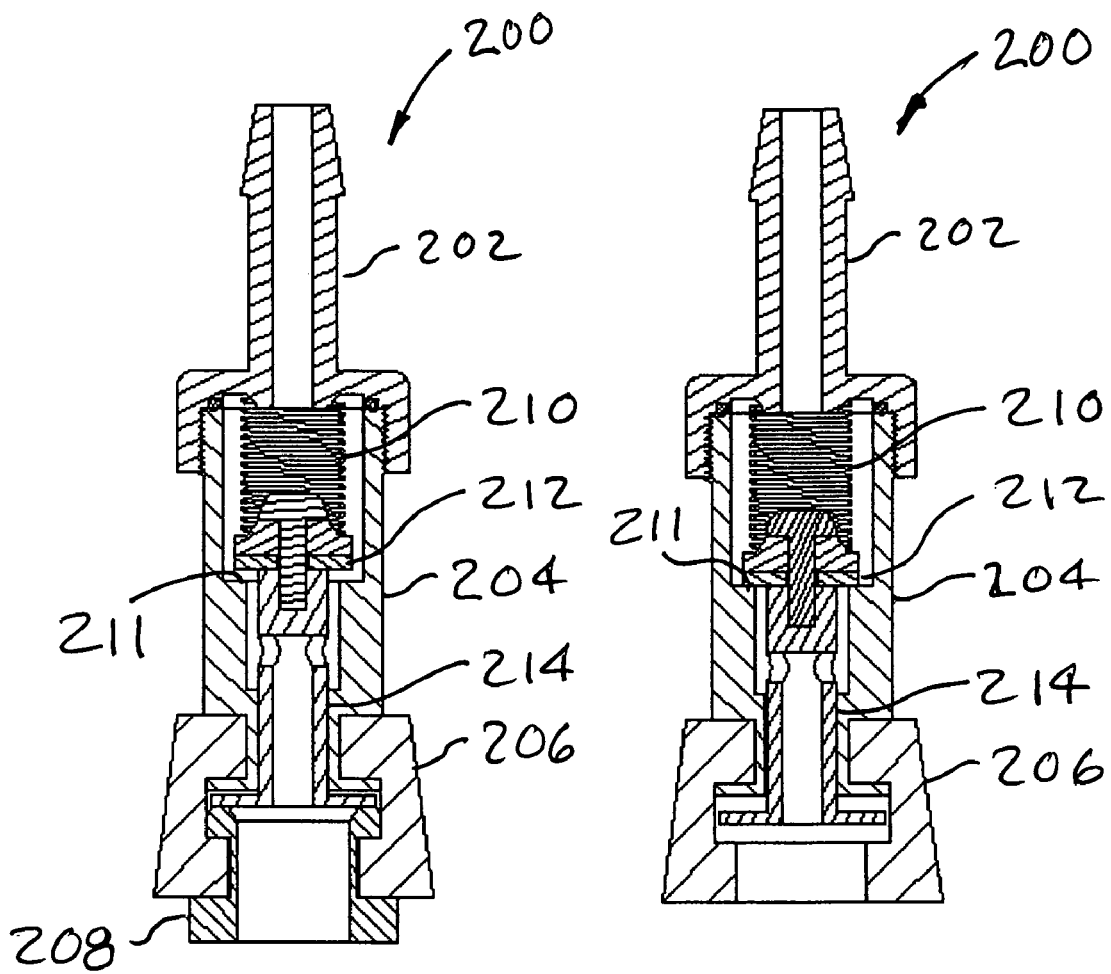
FIG. 14 is a section view of a full shutoff channel connector useful in the practice of the present invention, shown in an open position and connected to an endoscope fitting.
FIG. 15 is a section view of the channel connector of FIG. 14, shown in a disconnected and closed position.
Figure 16:
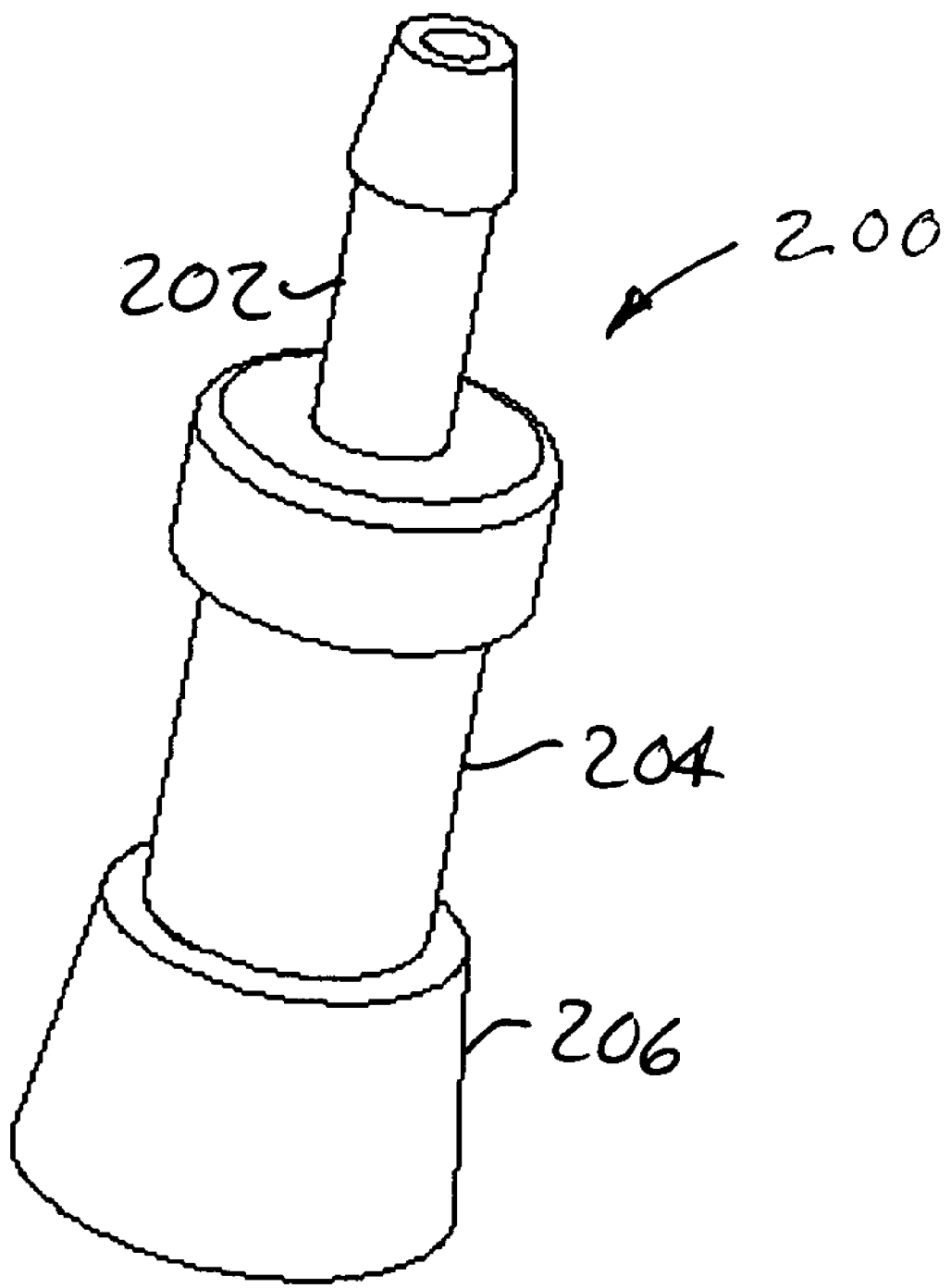
FIG. 16 is an exterior perspective view of the channel connector shown in FIGS. 14 and 15.

One manufacturer of shutoff connectors is the Colder Products Company, of 1001 Westgate Drive, St. Paul, Minn. 55114, which offers a PMC12 series of shutoff connectors. Another full shutoff connector 200 useful in the practice of one embodiment of the present invention is shown in FIGS. 14, 15 and 16. The connector 200 has a barbed hose cap 202 threaded on a body 204 which carries a seal and retainer member 206 (similar or identical to the biopsy connector 82 shown in FIG. 2 received over the biopsy channel fitting 208, shown in FIGS. 3 and 4 and as an example endoscope fitting in FIG. 14) formed of a resilient material that may be placed over a fitting 208 on an endoscope 36. When the connector 200 is disconnected from the endoscope 36, a spring 210 urges a seal 212 against a seat 211 in the body 204, blocking flow with respect to the cap 202 and any hose or tubing connected thereto, which is understood to be connected to the reprocessor 30 in operation. When the connector 200 is connected to the endoscope 36, endoscope fitting 208 urges plunger 214 against spring 210, lifting seal 212 from seat 211 and opening the fluid flow path through the connector 200.

Full shutoff connector 200 is useful with the configuration 87 for non-interconnected large channels. With that configuration, connector 200 has cap 202 connected to the connection block 38 via a flexible tube 54 and retainer member 206 is to be received over and sealed to an endoscope fitting 208.

Figure 13:
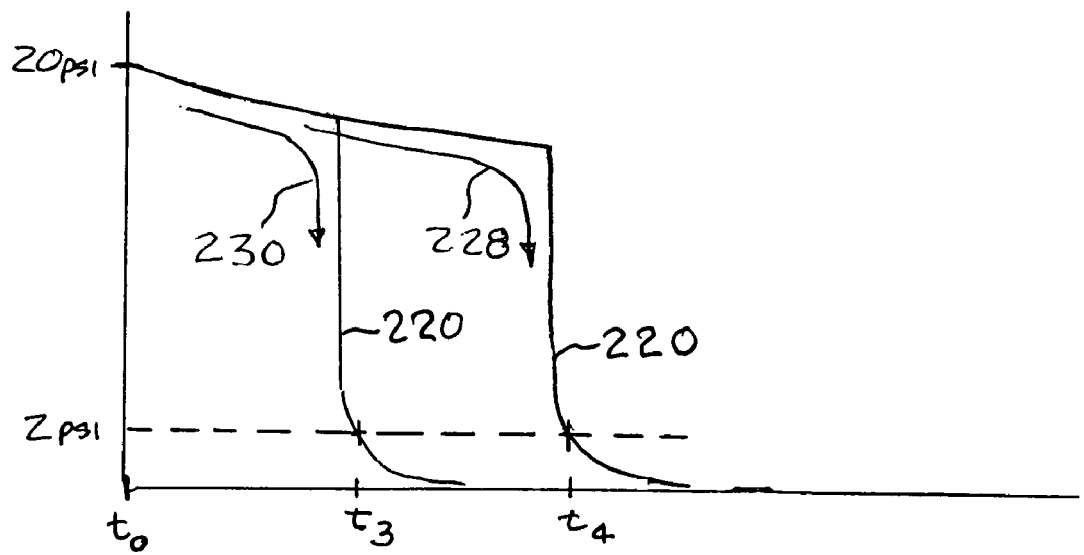
FIG. 13 is a pressure versus time waveform illustrating further aspects of the alternative embodiment of the present invention.

Using the connector 200 in the configuration 87 with a non-interconnected large channel, and practicing the present invention according to the first embodiment wherein a gaseous fluid is delivered via feed line 77, a connected and open condition will be indicated by a rapid decay response of curve 220 as indicated in FIG. 12, while a disconnected condition will be indicated by no decay or a relatively slow decay as indicated by curve 226 in FIG. 13.

Using the connector 200 in the configuration 87 with the second embodiment of pumping water or another liquid into the channel 76 and measuring back pressure can be accomplished by charging the channel 76 with liquid, then closing valve 70 and monitoring for pressure decay. If there is a decay, the channel is connected and open; if there is no decay, the channel is either disconnected or blocked, and must be corrected before continuing reprocessing the endoscope. Alternatively, another pressure switch or sensor may be used on feed line 77 to monitor a stalled head condition for the pump which results in a higher than operating pressure condition. With this approach, normal operating pressure sensed as back pressure indicates a connected and open channel; higher than normal operating pressure indicates that the pump is driving into a closed channel, indicating disconnection or blockage.

The alternative embodiment of the present invention mentioned above which uses a liquid (preferably water) "slug" or charge in the channel under test in connection with the gaseous fluid decay sensor system is described here in more detail. This embodiment is useful with the large channel configurations 85 and 87.

Figure 11:
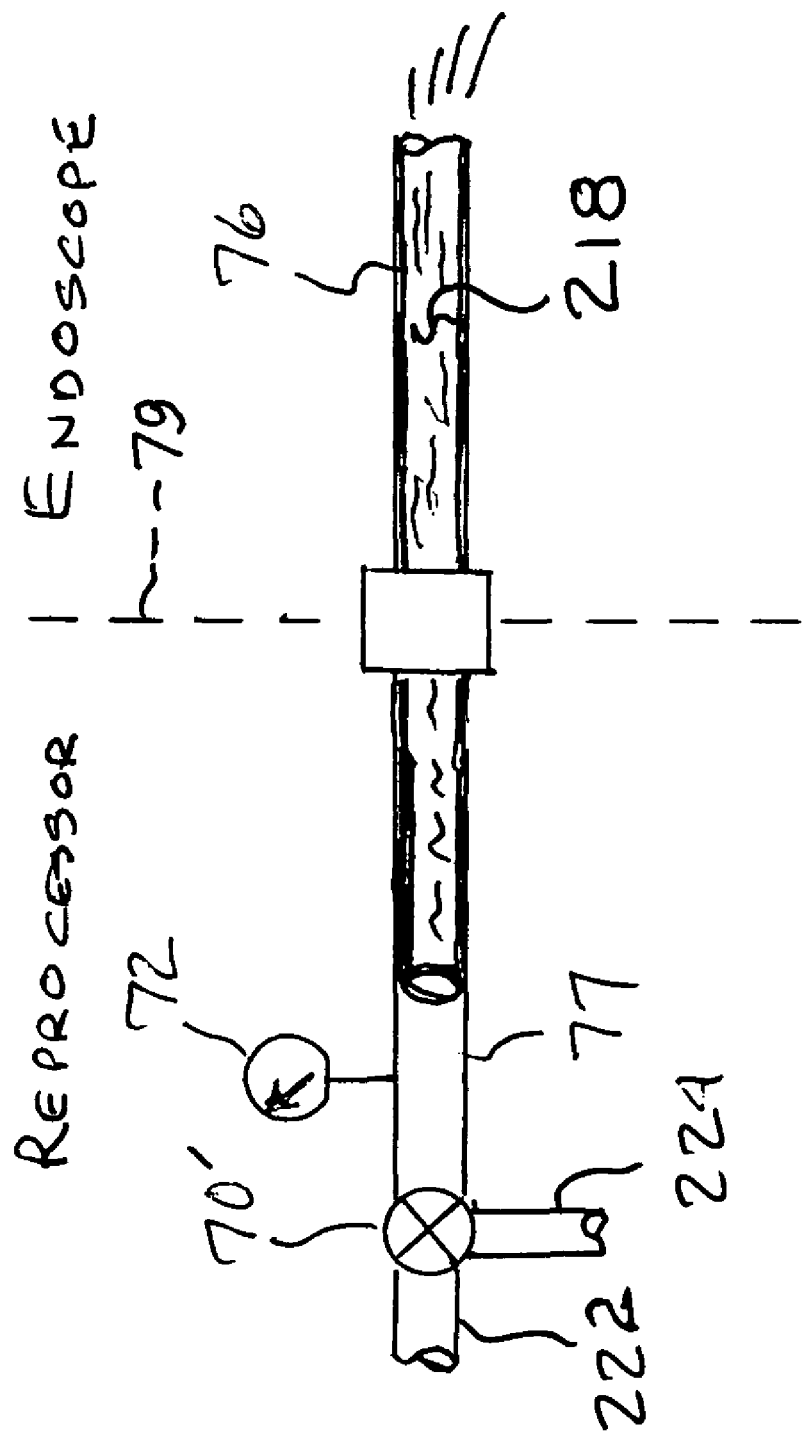
FIG. 11 is simplified schematic flow path illustrating application of an alternative embodiment of the present invention to a non-interconnected large channel.

Referring now to FIG. 11, feed line 77 may be connected to a source of liquid, preferably water, through conduit 222 to fill the reprocessor feed line 77 and the endoscope large channel 76 to which it is connected (or supposed to be connected) with a liquid slug 218 after which air is delivered via conduit 224 via a directional valve 70' through feed line 77 to large channel 76. The characteristic curves will now appear as in FIG. 13, with sequence 228 representing a connected condition and sequence 230 representing a disconnected condition. If the channel 76 is disconnected from the reprocessor, the water will discharge according to sequence 230 and follow curve 220 at time $t_3$, with the time from $t_0$ to $t_3$ representing the time to clear the water (or other liquid) slug 218 out from the feed line 77 (see e.g., configuration 87 in FIG. 5). If the channel 76 is connected, the water slug will be discharged from distal end 75 at time $t_4$, later than time $t_3$. The incremental times between times $t_0$, $t_3$, $t_4$ and $t_5$ can be considered delay times and allow discrimination between the disconnected and connected conditions because of the differences in the mass of water propelled by the air pressure and length of channel through which the water is moved between disconnected and connected conditions. Time $t_4$ represents the time of a switch closure on switch 98 (corresponding to pressure sensor 72 in FIG. 11) for a connected large channel 76. In the event large channel 76 is disconnected, time $t_3$ will be monitored and recorded by the control system, indicating a disconnection between the reprocessor 30 and the endoscope 36 at this channel. Similar to the operation with respect to configuration 83, this method may be used with large interconnected channels as in configuration 85, in addition to being useful in the large non-interconnected channel configuration 87. For configuration 85, liquid is either already present in the feed lines 77 and 77' or is purposely supplied, and is supplied to fill channels 76 out to the distal end 75. Once the configuration is filled with liquid, feed line 77 is opened to admit air using an arrangement similar to that of conduits 222 and 224 and directional valve 70' as shown in FIG. 11. Sensors 72 monitor the time for back pressure to drop to the predetermined level (e.g., 2 psi) and the system can discriminate between a disconnected condition (when sequence 230 occurs with curve 220 sensed at time $t_3$), or a connected and open condition (when sequence 228 occurs and curve 220 is sensed at time $t_4$).

This invention is not to be taken as limited to all of the details thereof as modifications and variations thereof may be made without departing from the spirit or scope of the invention.

What is claimed is:

1. A method of detecting connectivity between an automatic reprocessor and a channel in an endoscope undergoing reprocessing using the automatic reprocessor, the method comprising:
   a. providing a source of pressurized fluid;
   b. directing the pressurized fluid to a channel in an endoscope;
   c. discontinuing pressurizing the fluid;
   d. monitoring the back pressure in the pressurized fluid; and
   e. determining whether the channel is connected and open or is disconnected by monitoring the time after commencement of step c for actual back pressure to fall to a predetermined value, wherein the predetermined value is a stored pressure value that is measured prior to step b and is specific to the channel for which connectivity is being detected, and wherein the predetermined value is stored with a set of predetermined values that includes different pressure values specific to different channels.

2. The method of claim 1 wherein the source of pressurized fluid is a tank.

3. The method of claim 1 wherein the source of pressurized fluid is a pump.

4. The method of claim 1 wherein the fluid is a gas.

5. The method of claim 4 wherein the gas is air.

6. The method of claim 4 wherein a liquid is supplied to the channel before the pressurized gas is supplied to the channel.

7. The method of claim 6 wherein the liquid includes water.

8. The method of claim 7 wherein step e further comprises determining the channel is disconnected when the time for the actual back pressure to fall to the predetermined value is less than a first predetermined time.

9. The method of claim 8 wherein step e further comprises determining the channel is connected and open when the time for the actual back pressure to fall to the predetermined value is greater than the first predetermined time.

10. The method of claim 1 wherein step e further comprises determining the channel is disconnected when the time for the actual back pressure to fall to the predetermined value is less than a first predetermined time.

11. The method of claim 1 wherein step e further comprises determining the channel is connected and open when the time for the actual back pressure to fall to the predetermined value is between a first predetermined time and a second predetermined time.

12. A method of determining connectivity between an automatic reprocessor and a channel in an endoscope undergoing reprocessing using the automatic reprocessor, the method comprising:
   a. providing a source of pressurized fluid;

b. directing the pressurized fluid to a specific channel and model of endoscope under test;
c. discontinuing pressurizing the fluid directed to the channel under test;
d. monitoring the decay of back pressure in the channel under test; and
e. determining whether the channel is connected and open or is disconnected by comparing the time for the pressure in the channel under test to decay to a predetermined level to one or more predetermined times specific to the channel wherein the one or more predetermined times are stored discharge times characteristic to the channel for which connectivity is being detected, and wherein the one or more predetermined times are stored with a set of predetermined times that includes different stored discharge times characteristic to different channels.

13. The method of claim 12 further comprising:
e. providing an indication that the channel under test is disconnected if the time for the pressure in the channel under test to decay to a predetermined level is less than a first predetermined time.

14. The method of claim 13 further comprising:
f. providing an indication that the channel under test is connected and open if the time for the pressure in the channel under test to decay to a predetermined level is greater than the first predetermined time and less than a second predetermined time.

15. A method of determining whether interconnected channels in an endoscope are connected to a reprocessor comprising the steps of:
a. directing pressurized fluid into one of the interconnected channels;
b. monitoring back pressure from the pressurized fluid in at least one other of the interconnected channels; and
c. comparing the monitored back pressure to a predetermined back pressure that is indicative of proper connection to determine whether the interconnected channels are connected to the reprocessor.

16. The method of claim 15, wherein the interconnected channels are connected if the monitored back pressure exceeds the predetermined back pressure, and wherein at least one of the interconnected channels is blocked or not properly connected if the monitored back pressure does not exceed the predetermined back pressure.

17. A method of determining whether a large channel in an endoscope is connected to a reprocessor comprising the steps of:
a. providing a shut off connector in a fluid path between a large channel in the endoscope and a reprocessor wherein the shut off connector
   i. blocks fluid flow when the large channel is disconnected from the reprocessor, and
   ii. enables fluid flow when the large channel is connected to the reprocessor;
b. providing a source of pressurized fluid in the reprocessor directed to the fluid path;
c. discontinuing pressurizing the fluid path in the reprocessor;
d. monitoring the back pressure in the fluid path; and
e. determining whether the large channel is connected and open or is disconnected by monitoring a characteristic of the pressure in the fluid path and comparing the characteristic of the pressure to a predetermined value, wherein the predetermined value is measured prior to ste b and is specific to the channel for which connectivity is being detected, and wherein the predetermined value is stored with a set of predetermined values that includes different predetermined values specific to different channels.

18. The method of claim 17 wherein the characteristic of the pressure comprises a level of the pressure in the fluid path.

19. The method of claim 17 wherein the characteristic of the pressure comprises a time to decay to a predetermined level of pressure in the fluid path.

20. The method of claim 17 wherein the characteristic of the pressure comprises a delay time to a decay time for the pressure in the fluid path.

* * * * *

UNITED STATES PATENT AND TRADEMARK OFFICE
CERTIFICATE OF CORRECTION

| | | |
|---|---|---|
| PATENT NO. | : 7,901,349 B2 | Page 1 of 1 |
| APPLICATION NO. | : 11/264909 | |
| DATED | : March 8, 2011 | |
| INVENTOR(S) | : Paul T. Feld et al. | |

It is certified that error appears in the above-identified patent and that said Letters Patent is hereby corrected as shown below:

column 10, line 26, delete "ste" and insert therefor --step--

Signed and Sealed this
Tenth Day of May, 2011

David J. Kappos
*Director of the United States Patent and Trademark Office*